United States Patent [19]

Goyal et al.

[11] Patent Number: 5,919,631

[45] Date of Patent: *Jul. 6, 1999

[54] METHOD OF DETERMINING THE DEGREE OF AGGREGATION OF THE β-A4 PEPTIDE

[75] Inventors: Shefali Goyal, Warren, N.J.; Joseph W. Paul, Winterville, N.C.; Norbert G. Riedel, Bedminster; Sudhir R. Sahasrabudhe, Whippany, both of N.C.

[73] Assignee: Hoechst Marion Roussel, Inc., Bridgewater, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/682,245

[22] Filed: Jul. 17, 1996

[51] Int. Cl.⁶ .................................................. G01N 33/53
[52] U.S. Cl. ........................... 435/7.1; 436/164; 436/171
[58] Field of Search .................................. 435/4, 7.1, 7.8; 436/536, 537, 538, 539, 540, 164, 86, 171; 530/300, 324, 418

[56] References Cited

FOREIGN PATENT DOCUMENTS

| | | |
|---|---|---|
| 0281922 | 9/1988 | European Pat. Off. . |
| 9316101 | 8/1993 | WIPO . |
| 9505604 | 2/1995 | WIPO . |
| 9512815 | 5/1995 | WIPO . |

OTHER PUBLICATIONS

Sedmak, et al., Analytical Biochemistry 79, pp. 544–552, (1977).
Jarrett, et al., Cell, vol. 73, pp. 1055–1058 (1993).
Compton, et al., Analytical Biochemistry 151, pp. 369–374 (1985).
D.J. Selkoe, Scientific American, pp. 68–78 (1991).
M.M. Bradford, Analytical Biochemistry 72, pp. 248–254 (1976).
H. LeVine, Protein Science 2, pp. 404–410 (1993).
G. Perry et al., Brain Researach, vol. 420, pp. 233–242 (1987).

*Primary Examiner*—Patricia A. Duffy
*Attorney, Agent, or Firm*—Frommer Lawrence & Haug LLP

[57] ABSTRACT

A method of determining the degree of aggregation of the βA4 peptide is disclosed. The method comprises reacting the protein with a suitable binding agent which is capable of binding the βA4 peptide only in its non-aggregated state to form an amount of protein bound binding reagent. The amount of protein bound binding agent is then measured.

4 Claims, 2 Drawing Sheets

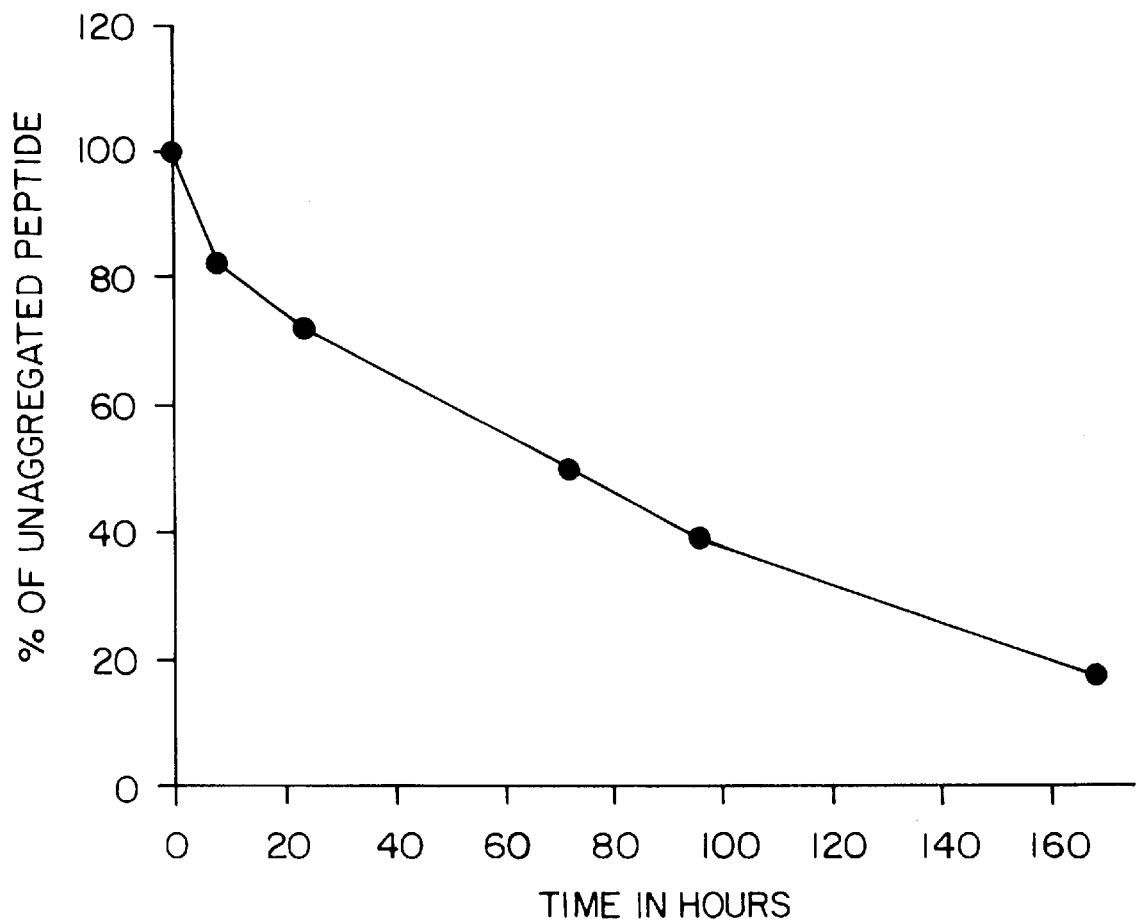

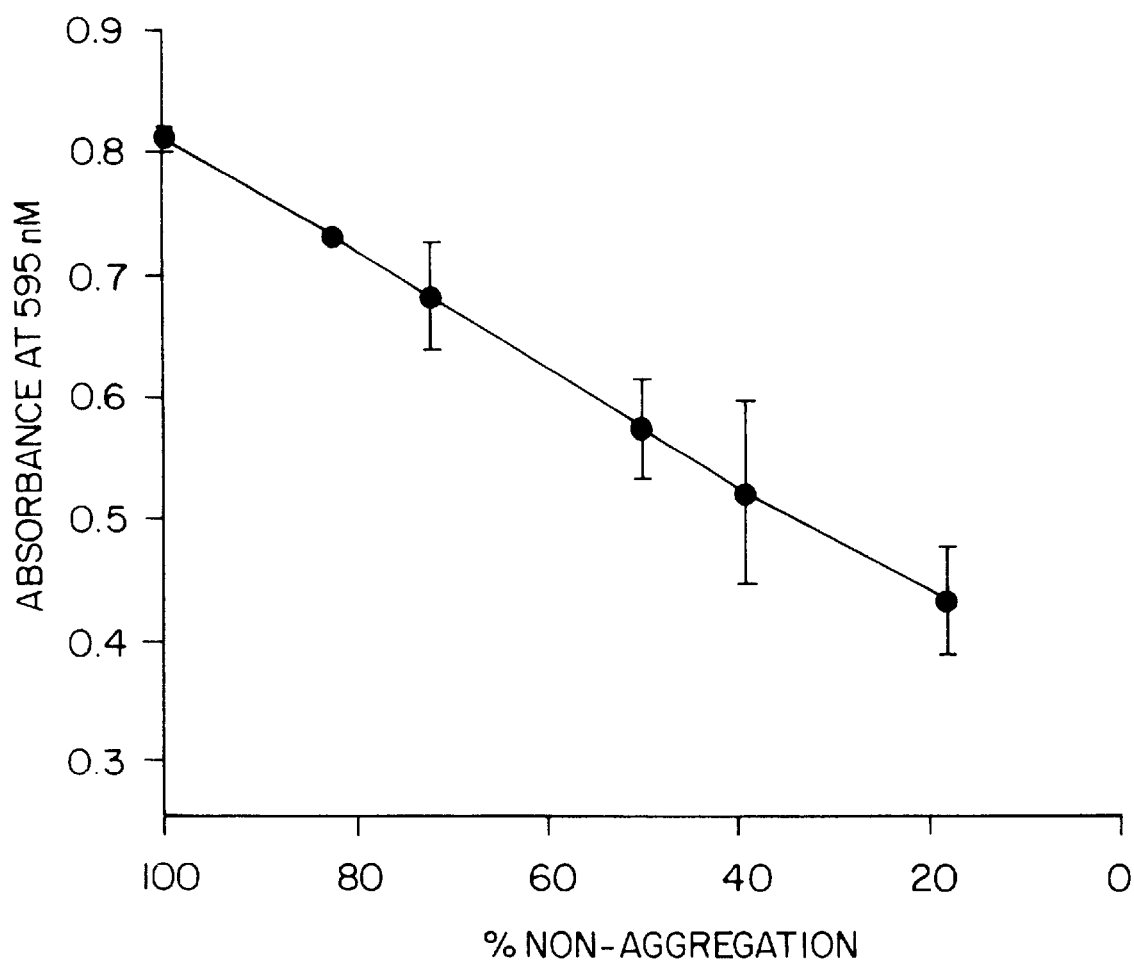

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 39 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

Asp Ala Glu Phe Arg His Asp Ser Gly Tyr Glu Val His His Gln Lys
   1             5                   10               15

Leu Val Phe Phe Ala Glu Asp Val Gly Ser Asn Lys Gly Ala Ile Ile
                20                25               30

Gly Leu Met Val Gly Gly Val
            35

(2) INFORMATION FOR SEQ ID NO:2:

(i) SEQUENCE CHARACTERISTICS:
      (A) LENGTH: 40 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:2:

Asp Ala Glu Phe Arg His Asp Ser Gly Tyr Glu Val His His Gln Lys
   1             5                   10               15

Leu Val Phe Phe Ala Glu Asp Val Gly Ser Asn Lys Gly Ala Ile Ile
                20                25               30

Gly Leu Met Val Gly Gly Val Val

```
                    35                  40

(2) INFORMATION FOR SEQ ID NO:3:

(i) SEQUENCE CHARACTERISTICS:
        (A) LENGTH: 41 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Asp Ala Glu Phe Arg His Asp Ser Gly Tyr Glu Val His His Gln Lys
    1               5                   10                  15

Leu Val Phe Phe Ala Glu Asp Val Gly Ser Asn Lys Gly Ala Ile Ile
                    20                  25                  30

Gly Leu Met Val Gly Gly Val Val Ile
                    35                  40

(2) INFORMATION FOR SEQ ID NO:4:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Asp Ala Glu Phe Arg His Asp Ser Gly Tyr Glu Val His His Gln Lys
    1               5                   10                  15

Leu Val Phe Phe Ala Glu Asp Val Gly Ser Asn Lys Gly Ala Ile Ile
                    20                  25                  30

Gly Leu Met Val Gly Gly Val Val Ile Ala
                    35                  40

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Gln Lys Leu Val Thr Thr Ala Glu
    1               5
```

METHOD OF DETERMINING THE DEGREE OF AGGREGATION OF THE β-A4 PEPTIDE

BACKGROUND OF THE INVENTION

1. Field of the Invention

This invention relates of a method of determining the degree of aggregation of the βA4 peptide (SEQ ID NO:1–4) and more particularly to detecting the protein by reacting the protein with a suitable binding reagent and measuring the amount of resultant unreacted binding reagent.

2. Discussion of the Prior Art

It is known that the brain of patients having Alzheimer's Disease contains aggregations or clumps of a small fragment of the beta-amyloid precursor protein which fragment is known as the amyloid beta-peptide or the βA4 peptide. The 42-mer peptide sequence of the βA4 peptide (SEQ ID NO:1–4) is Aspartate-Alanine-Glutamate-Phenylalanine-Arginine-Histidine-Aspartate-Serine-Glycine-Tyrosine-Glutamate-Valine-Histidine-Histidine-Glutamine-Lysine-Leucine-Valine-Phenylalnine-Phenylalanine-Alanine-Glutamate-Aspartate-Valine-Glycine-Serine-Aspargine-Lysine-Glycine-Alanine-Isoleucine-Isoleucine-Glycine-Leucine-Methionine-Valine-Glycine-Glycine-Valine-Valine-Isoleucine-Alanine. (DAEFRHDSGYEVHHQKLVFFAEDVGSNKGAIIGLMVGGVVIA) (SEQ ID:4).

For a general discussion on the βA4 peptide (SEQ ID NO:1–4) and Alzheimer's Disease, reference is made to Dennis J. Selko, *Scientific American*, November 1991, 68–78, and Joseph T. Jarrett et al., *Cell*, Vol. 73, 1055–1058 (1993).

A potential treatment for combating the progress of Alzheimer's Disease is to use a drug comprising an active ingredient which prevents the aggregation or clumping of the βA4 peptide. Accordingly, a screening test for identifying such active ingredient or effective chemical compound is needed.

There are various assays known in the art for detecting proteins per se. One such assay involves the use of Bradford dye, or as it is also known as Coomassie Brilliant Blue G250. In this regard, reference is made to J. James Sedmak et al., *Analytical Biochemistry*, 79, 544–552 (1977), which describes an assay for proteins but not for the A4 peptide whether in the aggregate or free state.

What is required and desired is an assay for the βA4 peptide which distinguishes such protein in the aggregate state from when it is in the free or unaggregated state and reflects the effect of various compounds on such aggregate state. In this regard, H. LeVine, *Protein Science*, 2, 404–410 (1993) describes the detection of aggregated amyloid employing Thioflavin T.

BRIEF DESCRIPTION OF THE DRAWING

FIG. 1 illustrates the degree of non-aggregation of the βA4 peptide over time.

FIG. 2 illustrates the degree of non-aggregation of the βA4 peptide in terms of a measurable characteristic of the degree of non-aggregation.

SUMMARY OF THE INVENTION

This invention relates to a method of determining the degree of aggregation of the βA4 peptide and more particularly, the method which comprises reacting the protein with a suitable binding agent which is capable of binding the βA4 peptide only in its non-aggregated state to form an amount of protein bound binding reagent. The amount of the protein bound binding agent is then measured.

DETAILED DESCRIPTION

It is known that the brain of Alzheimer's disease patients as compared to the brain of non-Alzheimer's disease individuals, have present an amyloid protein of 39–42 amino acids known as the βA4 peptide. The 39-mer peptide sequence of the βA4 peptide is DAEFRHDSGYEVHHQKLVFFAAEDVGSNKGAIIGLMVGGV (SEQ ID NO:1). The 40-mer peptide sequence of the βA4 peptide is DAEFRHDSGYEVHHQKLVFFAAEDVGSNKGAIIGLMVGGVV (SEQ ID NO: 2). The 41-mer peptide sequence of the βA4 peptide is DAEFRHDSGYEVHHQKLVFFAAEDVGSNKGAIIGLMVGGVVI (SEQ ID NO:3). This protein clumps or aggregates in the brain of such Alzheimer's Disease patients whereby the aggregated protein may be responsible for the destruction of normal brain cells. Once the killing clumps or aggregates form, the formation is almost irreversible. Accordingly, a potential treatment of Alzheimer's disease is to treat a patient with a compound or drug which prevents the clump or aggregation of the βA4 peptide.

It has been discovered that potential compounds for treatment of Alzheimer's disease can be identified by a screening test which indicates whether the compounds which are selected as candidates do or do not inhibit the aggregation of the βA4 peptide in vitro.

A suitable binding reagent is selected. A suitable binding reagent is one which selectively reacts with either the non-aggregated amyloid peptide, i.e. βA4, or the aggregated amyloid peptide but not with the candidate compound is being screened, and which in its reacted form, i.e. reacted with the peptide, exhibits a measurable characteristic, e.g. light absorbance at a particular wavelength. Some suitable binding reagents include Bradford dye, or Coomassie Brilliant Blue G250, Congo Red and Thioflavin T. A particularly suitable binding reagent is the Bradford dye. Bradford dye is Coomassie Brilliant Blue G250. Bradford dye or Coomassie blue dye is described by M. Bradford, *Anal. Biochem.*, 72, 248 (1976); A. H. Reisner et al., *Anal. Biochem.*, 64, 509 (1975); S. Fazukes de St. Groth, et al., *Biochim. Biophys. Acta*, 71 377 (1963) and J. J. Sedmack et al., *Anal. Biochem*, 79, 544 (1977), and is commercially available as a standard reagent, (e.g. Protein Assay Dye Reagent Concentrate available from Bio-Rad Life Science Group, Hercules, Calif.). This dye reacts only with non-aggregated βA4 and not with any aggregates of this amyloid peptide.

The Bradford dye has been described, as indicated above, by Marion M. Bradford in *Analytical Biochemistry*, 72, 248–254 (1976), as 0.01% (weight/volume) (w/v) Coomassie Brilliant Blue G-250, 1.7% (w/v) ethanol, and 8.5% (w/v) phosphoric acid. The Protein Assay Dye Reagent Concentrate, commercially available from Bio-Rad as catalog number 500-0006, is a modified version of the Bradford dye with approximately 0.04% (w/v) Coomassie Brilliant Blue G-250 dissolved in 25% methanol, 50% phosphoric acid and 25% water. The modifications render it more stable, with longer shelf-life, and less bio-hazardous due to decreased phosphoric acid content, without adversely affecting its protein binding properties. It is also available in a kit form with one of two standards, as Kit I (with bovine gamma globulin) catalog number 500-0001, or as Kit II (with bovine serum albumin) catalog number 500-0002.

In practice a known concentration of amyloid peptide, i.e. A4 peptide, in its non-aggregated form, is prepared. The βA4 amyloid peptide in its non-aggregated state is obtained by peptide synthesis using a conventional peptide synthesizer, e.g. a Millipore Model 9050 peptide synthesizer. For example 10 milligrams of peptide is dissolved in a suitable organic solvent such as dimethylsulfoxide (DMSO) or acetonitrile at a suitable temperature, e.g. 20 to 25° C., to form a stock solution, e.g. 2,500 μM. The stock solution, is typically diluted, e.g. ten-fold, in phosphate-buffered saline (pH 7.4) to make a control solution, e.g. of 250 μM. A first aliquot, e.g. 16 μl, of the control solution is taken, typically with 144 μl of the phosphate buffered saline, and reacted with typically 25 μl of suitable binding reagent, e.g. Bradford dye, whereby the binding reagent reacts with the non-aggregated amyloid protein to form a first concentration or amount of protein bound binding reagent. The reaction with the binding agent is conducted under conditions whereby the binding agent will selectively bind only to the non-aggregated protein. Accordingly, the reaction conditions will be dictated by the particular binding agent employed and what binding characteristic is to be measured. For example, where Bradford dye is employed the binding reaction is typically carried out at a temperature of 20 to 25° C. for 5 to 15 minutes in a neutral or slightly basic ambient, that is at a pH ranging from 7.0 to 7.4.

It is to be noted that the first concentration or amount of protein bound binding reagent is measured by a suitable detecting means which is dependent upon the characteristic which the reacted binding agent exhibits, e.g. 0.7 absorbance at a wavelength of 595 nm for Bradford dye, to give a first value $X_1$.

A second aliquot of the control solution is selected. Since aggregation of βA4 occurs with time, the second aliquot is allowed to incubate at a suitable temperature, e.g. about 37° C., for a suitable time period, e.g. 24 to 72 hours, to form aggregates thereof, whereafter the binding reagent is added thereto and reacts only with the non-aggregated amyloid peptide to form a second concentration or amount of protein bound or reacted binding reagent. The aggregated concentration or amount of amyloid peptide does not react with the binding agent and thus is not detected and measured. Again, the amount of protein bound binding agent is measured, e.g. by absorbance spectroscopy at a suitable wavelength, e.g. 595 nm for Bradford dye, at room temperature to obtain a second value $X_2$, representing the amount of binding reagent which has reacted with the non-aggregated amount of βA4.

As aggregation occurs, the concentration of protein bound or reacted binding reagent is inverse to the degree of aggregation which has occurred. Accordingly, the second value $X_2$ is less than $X_1$, indicating that a certain degree of aggregation of the A4 peptide has occurred.

For purposes of a qualitative screen for candidate Alzheimer's compounds, a third equal aliquot of the control solution is taken. The third aliquot is again allowed to incubate under suitable conditions in the presence of candidate compound, e.g. for 48 hours at 37° C., whereafter the suitable binding agent, e.g. Bradford dye, is added thereto and the resultant solution or mixture is measured, e.g. spectroscopically with a conventional spectrophotometer, to obtain a value of bound binding reagent. If the candidate compound has no anti-aggregating effect then the measured value $X_3$, will approximately be equal to the second value, $X_2$. If on the other hand the third value $X_3$ exhibits a thirty to forty percent (30–40%) increase over that of $X_2$ then the candidate compound is considered to be a compound which inhibits aggregation of the amyloid peptide.

In carrying out the above-screening tests, the concentration of amyloid peptide to selected binding reagent should typically range from 1500 to 1800 (amyloid peptide/binding reagent). The concentration of amyloid peptide to candidate compound should typically range from 4 to 40 times or fold (candidate compound/amyloid peptide).

The degree of aggregation can be quantitatively determined in the following manner. Equal aliquots of the control solution are first incubated for various time periods. As the time increases the degree of aggregation increases. The binding agent, e.g. Bradford dye, is added after each time period and the measurement is made, e.g. measuring absorbance at a wavelength of 595 nm for Bradford dye. Thereafter the concentration or percentage of aggregated amyloid protein versus non-aggregated amyloid protein is determined for each time period. The binding agent measures the non-aggregated (or aggregated) protein. The amount of aggregation of β-amyloid is calculated by subtracting this number from the fresh protein (unaggregated, $X_1$) and expressed as a percentage. A linear inverse plot of percentage of aggregated peptide is obtained over various time periods, e.g. 24, 48, 72, 96 hours as typically shown in FIG. 1. The procedure is repeated except that after each incubation period the binding agent is added to the incubated aliquot and the resultant mixture is measured to determine the X values. Thereby a correlation between aggregation or non-aggregation can then be established, in terms of an X value, in relation to the spectroscopic reading, e.g. absorbance at a wavelength of 595 nm for Bradford dye as illustrated by FIG. 1. A standard plot is then obtained of X reading to percent of non-aggregation whereby the percent of aggregation is inversely obtained, as typically illustrated by FIG. 1.

The X values for a particular candidate compound can then be quantitatively determined in terms of percent inhibition of aggregation by comparison with the control, as typically illustrated in FIG. 2.

EXAMPLE 1

β-amyloid (also known as (βA-4) peptide was dissolved in 100% dimethylsulfoxide (DMSO) at 10 mg/ml (or 2500 μM) concentration. The resultant solution was diluted to 1 mg/ml (or 250 μM) stock in Phosphate Buffered Saline (PBS), pH 7.4, just prior to setting up the assay and dispensed in individual sample wells of a Corning 96-well plate at 16 μl per well (i.e. a final concentration of 25 μM). All treatments were done in triplicate.

In this example, the candidate compound was added to the test wells at three different concentrations (250 μM, 500 μM and 1 mM). Total volume in each well was brought up to 160 μl with PBS. For untreated control wells, no compound was added to the β-amyloid peptide, and the total volume was made to 160 μl with PBS. The plates were sealed with parafilm and incubated at 37° C. for 48 hours.

At the end of the incubation period, the plates were taken out and 25 μl of Bio-Rad protein assay dye reagent (Bradford dye) was added to all the wells with samples. A standard curve was also set up at this time for estimation of fresh (also considered as unaggregared) peptide absorbance. The dye was mixed by pipeting and the plates quickly spun at 2500 rpm to remove bubbles.

The Absorbance was read at 595 nm in a Dynatech MR5000 plate reader 15 minutes after adding the dye. The percent decrease in aggregation of β-amyloid due to the addition of candidate compound A41920t which is a 8-mer peptide of sequence Glutamine-Lysine-Leucine-Valine- Threonine-Threonine-Alanine-Glutamate (QKLVTTAE) (SEQ ID NO:5) was calculated from the difference between untreated aggregated peptide and the treated aggregated peptide. The percent decrease found was 48.1% with 250 µM of A41920t, 52.44% with 500 µM and 32.26% with 1 µM (or 1000 µM).

EXAMPLE 2

The procedure of Example 1 was repeated except that hydrogen peroxide (10 µl of 30% stock) was added to the wells in a 96-well plate with 16 µl of the 1 mg/ml β-amyloid stock. The final volume was then brought up to 160 µl by adding 134 µl of PBS to these wells. The plate was sealed and incubated at 37° C. for 48 hours.

At the end of the incubation period, the plates were taken out and 25 µl of Bio-Rad protein assay dye reagent (Bradford dye) was added to all the wells with samples as in Example 1. A standard curve was again used for estimation of fresh (also considered as unaggregated) peptide absorbance. The dye was mixed by pipeting and the plates quickly spun at 2500 rpm to remove bubbles.

The absorbance was read at 595 nm in the Dynatech MR5000 plate reader 15 minutes after adding the dye. The amount of aggregation was estimated by subtracting background and taking the difference between the fresh and hydrogen peroxide treated β-amyloid readings. The difference was expressed as percent over fresh or unaggregated peptide. The percentage of aggregation found was 97.7% after 48 hrs.

EXAMPLE 3

The procedure of Example 2 was repeated except that the glycoseamine glycan, pentosan polysulfate was substituted for hydrogen peroxide. The percentage of increase of aggregation found was 40.8% with 0.5 µM, 57.1% with 5 µM and, 62.9% with 50 µM.

EXAMPLE 4

The procedure of Example 1 was repeated except that 1-(5'-oxohexyl)-3-methyl-7-propyl-2,6-(1H,3H)-purinedione, also known as propentofylline was substituted for A41920t. The percentage of decrease of aggregation found was 29.68% with 500 µM and 37.4% with 1 mM (or 1000 µM).

---

We claim:

1. A method of determining in solution the degree of aggregation of a βA4 peptide (SEQ ID NO:4) which comprises:
   (a) reacting in solution a first sample containing non-aggregated βA4 peptide with Coomassie Brilliant Blue G 250 dye binding reagent which binds to the βA4 peptide only in its non-aggregated state to form at a first time period an amount of a protein bound binding reagent sample;
   (b) measuring said protein bound binding reagent sample to obtain a first measurement which correlates to the amount of protein bound binding reagent present;
   (c) repeating steps (a) and (b) above with a second sample at a second time period which differs from said first time period and in which aggregation of said peptide occurs to obtain a second measurement of the amount of protein bound binding reagent; and
   (d) determining the difference between said first measurement and said second measurement where said difference is a value which is inversely related to the degree of aggregation to determine the degree of aggregation.

2. A method of determining in solution a compound which inhibits the aggregation of a βA4 peptide (SEQ ID NO: 4) which comprises:
   (a) incubating a first sample containing non-aggregated βA4 peptide for a time period sufficient to form aggregates of said peptide;
   (b) reacting said incubated sample containing non-aggregated and aggregated βA4 peptide with Coomassie Brilliant Blue G 250 dye binding reagent which binds to the βA4 peptide only in its non-aggregated state to form a first amount of a protein bound binding reagent sample;

(c) measuring said protein bound binding reagent sample to obtain a first reference measurement which represents a value which is inverse to the degree of aggregation;

(d) repeating steps (a) and (b) and (c) above, except that said incubating is carried out with a second sample which is equal to said first sample in the amount of non-aggregated βA4 peptide in the presence of a selected candidate compound to form a second amount of a protein bound binding reagent sample to obtain a second reference measurement and;

(e) determining if said second reference measurement is greater than said first reference measurement to determine if said candidate compound inhibits the degree of aggregation.

3. A method of determining in solution the degree of aggregation of a βA4 peptide having the 42-mer sequence DAEFRHDSGYEVDAEFRHDSGYEVH-HQKLVFFAAEDVGSNKGAIIGLMVGGVVIA (SEQ ID NO: 4), which comprises:

(a) reacting in solution a first sample comprising at least the peptide sample in a non-aggregated state with Coomassie Brilliant Blue G-250 dye binding reagent to form at a first time period an amount $X_1$ of said peptide bound to said reagent;

(b) reacting in solution a second sample which is equal to said first sample, after a second time period, which is different than said first time period and during which a degree of aggregation of said peptide occurs, with said binding reagent to form an amount of $X_2$ of said peptide bound to said reagent; and (c) determining the value of the difference between $X_1$ and $X_2$ where said value is inverse to the degree of aggregation of the βA4 peptide to determine the degree of aggregation.

4. A method of determining a compound which inhibits the aggregation of a βA4 peptide comprising the 42-mer sequence DAEFRHDSGYEVDAEFRHDSGYEVH-HQKLVFFAAEDVGSNKGAIIGLMVGGVVIA (SEQ ID NO: 4), which comprises:

(a) reacting in solution a first sample containing at least the peptide in a non-aggregated state with a binding agent comprising Coomassie Brilliant Blue G-250 dye to form an amount $X_2$ of said non-aggregated peptide bound to said binding agent after a time period during which the peptide forms a degree of being in the aggregated state and where $X_2$ is a value which is inverse to the degree of aggregation;

(b) measuring said amount $X_2$;

(c) combining a second sample equal to said first sample, with a candidate compound to form a test sample;

(d) adding after said time period said binding agent to said test sample to form an amount $X_3$ of said protein bound to said binding agent where $X_3$ is a value which is inverse to the degree of aggregation;

(e) measuring said amount $X_3$; and (f) measuring the difference between $X_2$ and $X_3$ to determine any inhibition to the said degree of aggregation by said candidate compound.

* * * * *